(12) United States Patent
Zhang et al.

(10) Patent No.: US 9,875,829 B2
(45) Date of Patent: Jan. 23, 2018

(54) METHOD FOR RECOATING RTV ANTI-POLLUTION FLASHOVER COATING ON INSULATOR COATED WITH RTV ANTI-POLLUTION FLASHOVER COATING

(71) Applicants: STATE GRID SHANXI PROVINCE ELECTRIC POWER COMPANY JINZHONG SUPPLY COMPANY, Jinzhong, Shanxi (CN); Graduate School at Shenzhen, Tsinghua University, Shenzhen, Guangdong (CN)

(72) Inventors: Xuedong Zhang, Shanxi (CN); Ling Liu, Shanxi (CN); Hongwei Wang, Shanxi (CN); Liang'an Yao, Shanxi (CN); Qiang Xie, Shanxi (CN); Kai Sun, Shanxi (CN); Jingzhao Lu, Shanxi (CN); Zhidong Jia, Guangdong (CN); Can Chen, Guangdong (CN)

(73) Assignees: STATE GRID SHANXI PROVINCE ELECTRIC POWER COMPANY JINZHONG SUPPLY COMPANY, Jinzhong, Shanxi (CN); GRADUATE SCHOOL AT SHENZHEN, TSINGHUA UNIVERSITY, Shenzhen, Guangdong (CN)

( * ) Notice: Subject to any disclaimer, the term of this patent is extended or adjusted under 35 U.S.C. 154(b) by 0 days.

(21) Appl. No.: 15/170,498

(22) Filed: Jun. 1, 2016

(65) Prior Publication Data

US 2016/0276069 A1   Sep. 22, 2016

Related U.S. Application Data

(63) Continuation-in-part of application No. PCT/CN2014/001042, filed on Nov. 24, 2014.

(30) Foreign Application Priority Data

Dec. 2, 2013   (CN) .......................... 2013 1 0635119

(51) Int. Cl.
*H01B 19/04*   (2006.01)
*B05B 9/01*   (2006.01)
(Continued)

(52) U.S. Cl.
CPC ............... *H01B 19/04* (2013.01); *B05B 9/01* (2013.01); *B05D 3/12* (2013.01); *B05D 5/005* (2013.01);
(Continued)

(58) Field of Classification Search
None
See application file for complete search history.

(56) References Cited

U.S. PATENT DOCUMENTS

| 4,341,842 A | 7/1982 | Lampe |
| 4,476,155 A * | 10/1984 | Niemi ..................... C08L 83/04 174/137 A |
| 7,134,579 B2 | 11/2006 | Scheindel |

FOREIGN PATENT DOCUMENTS

| CN | 1876250 | 12/2006 |
| CN | 100998974 | 7/2007 |

(Continued)

OTHER PUBLICATIONS

International Search Report, issued in the corresponding International Application No. PCT/CN2014/001042, dated Feb. 27, 2015, 3 pages.
(Continued)

*Primary Examiner* — Michael P Rodriguez
(74) *Attorney, Agent, or Firm* — Hamre, Schumann, Mueller & Larson, P.C.

(57) ABSTRACT

Disclosed is a method for recoating an RTV anti-pollution flashover coating on an insulator coated with the RTV anti-pollution flashover coating. The insulator includes an insulator body, a steel cap connected to an upper surface of the insulator body, and a steel pin connected to a lower surface of the insulator body. The method includes: (1) wiping off dirt on a surface of the insulator; (2) determining whether the insulator can be recoated; (3) performing coating by using an RTV anti-pollution flashover coating with the content of solid being 55%-65%. After coating is performed, a newly coated anti-pollution flashover coating can be closely adhered to a surface of the insulator, swelling does not occur, adhesion of the coating with respect to the insulator is not reduced, the hydrophobicity of the surface is recovered, and non-reduction of a pollution flashover voltage of the insulator is ensured.

5 Claims, 2 Drawing Sheets

(51) Int. Cl.
  B05D 3/12    (2006.01)
  B05D 5/00    (2006.01)
  B05D 5/08    (2006.01)
  B08B 1/00    (2006.01)
  G01J 3/52    (2006.01)
  G01N 19/04   (2006.01)

(52) U.S. Cl.
  CPC ................ *B05D 5/08* (2013.01); *B08B 1/006* (2013.01); *G01J 3/52* (2013.01); *G01N 19/04* (2013.01)

(56) References Cited

FOREIGN PATENT DOCUMENTS

| CN | 102513284     | 6/2012 |
| CN | 103545068     | 1/2014 |
| CN | 103545068 A * | 1/2014 |
| CN | 103736645     | 4/2014 |
| CN | 103752488     | 4/2014 |
| DE | 119493        | 4/1976 |
| EP | 1013347       | 6/2000 |

OTHER PUBLICATIONS

Liang et al., "Study on RTV Aging Failure Treatment", Technology Exchange and Application, Feb. 25, 2011, pp. 65-67.

Zhang et al, Spray Painting Technology and Gist of Anti-pollution-flashover RTV Silicone Rubber, Jiangsu Electrical Engineering, vol. 31, No. 6, Nov. 2012.

Li et al., "Application Implementation of Aniti-flashover Coating for Polluted Electric Devices", Distribution & Utilization, No. 4, vol. 24, Aug. 2007.

* cited by examiner

METHOD FOR RECOATING RTV ANTI-POLLUTION FLASHOVER COATING ON INSULATOR COATED WITH RTV ANTI-POLLUTION FLASHOVER COATING

This application is a continuation in part of PCT/CN2014/001042, filed on Nov. 24, 2014. The contents of PCT/CN2014/001042 are all hereby incorporated by reference.

BACKGROUND

Technical Field

The present application relates to the processing of an insulator in a power system, and in particular, to a method for recoating an RTV anti-pollution flashover coating on an insulator coated with the RTV anti-pollution flashover coating.

Related Art

In a power system, using a room temperature vulcanized silicone anti-pollution flashover coating (RTV anti-pollution flashover coating for short) is a very important anti-pollution flashover measure. Coating an RTV anti-pollution flashover coating on a surface of an insulator can significantly improve the hydrophobicity of the insulator, and further increases a pollution flashover voltage of the insulator and prevents a pollution flashover accident. However, the RTV anti-pollution flashover coating has a relatively poor weather resistance performance, and aging of the RTV anti-pollution flashover coating occurs in a long-running process due to influences of factors such as electric field, light, and high humidity. Therefore, the hydrophobicity of a surface is reduced. In some heavily-polluted areas, the hydrophobicity is reduced or even disappears due to the excessive accumulation of dirt on the surface of the RTV anti-pollution flashover coating. In such cases, a commonly adopted measure is to replace the insulator, and to coat an RTV anti-pollution flashover coating on a surface of the newly replaced insulator. However, this processing measure causes high costs and a waste of insulators.

SUMMARY

The technical problem which the present application attempts to solve is that: in order to make up the deficiencies of the prior art, a method for recoating an RTV anti-pollution flashover coating on an insulator coated with the RTV anti-pollution flashover coating is provided, so as to recover the hydrophobicity of a surface of the insulator in a case of not replacing the insulator, and ensure that an anti-pollution flashover performance of the insulator is not reduced.

The technical problem of the present application is solved by using the following technical solution:

A method for recoating an RTV anti-pollution flashover coating on an insulator coated with the RTV anti-pollution flashover coating, wherein the insulator includes an insulator body, a steel cap connected to an upper surface of the insulator body, and a steel pin connected to a lower surface of the insulator body, wherein the method includes the following steps:

(1) wiping off dirt on a surface of the insulator;

(2) determining, according to a comprehensive evaluation of the hydrophobicity and adhesion of or a comprehensive evaluation of the hydrophobicity, color of the coating, and adhesion of an original coating of an RTV anti-pollution flashover coating on the surface of the insulator, whether the insulator can be recoated; and (3) applying coating as follows on an insulator that can be coated:

(3.1) when the insulator body and the position of a seam formed by connecting the steel cap and the upper surface of the insulator body are sprayed with the RTV anti-pollution flashover coating by using a spray gun, the pressure being 0.6±0.1 MPa, the distance between a nozzle of the spray gun and the surface to be sprayed of the insulator being 200±50 mm, the angle between an airflow axis and the surface to be sprayed being 70°-90°, and the standing time at the same position during spraying being 1-2 s; and (3.2) when the position of a seam formed by connecting the steel pin and the lower surface of the insulator body is sprayed with the RTV anti-pollution flashover coating by using a spray gun, the pressure being 0.6±0.1 MPa, the distance between a nozzle of the spray gun and the position of the seam being 100±30 mm, the angle between an airflow axis and the lower surface of the insulator body being 0°-20°, and the standing time at the same position during spraying being not greater than 1 s.

In steps (3.1) and (3.2), the mass content of solid of the recoated RTV anti-pollution flashover coating is 55%-65%, spraying is performed at least twice, and the thickness of a newly coated coating of the RTV anti-pollution flashover coating is not less than 0.2 mm.

When a surface of an original coating of an RTV anti-pollution flashover coating is recoated, a newly coated coating has a great influence on the original coating, and the original coating also has a great influence on a coating effect of the newly coated coating. In a spraying process of the present application, with regard to a recoated RTV anti-pollution flashover coating that is recoated by using process conditions of the foregoing technical solution, upon tests, the hydrophobicity thereof can achieve HC1-HC2, the adhesion level is ISO0-ISO2, and the total thickness (the sum of the thickness of the new coating and the thickness of the original coating) is not less than 0.35 mm. Meanwhile, an impact and a swelling damage to the original coating caused by a recoating process is avoided, for example, if a spraying pressure is excessively high, the excessively high pressure causes an impact on a surface of the original coating, affects adhesion of the original coating with respect to an insulator, and further affects adhesion of a coating of the newly coated RTV anti-pollution flashover coating; if a pressure is excessively low, the excessively low pressure affects a spraying effect; if the standing time at the same position is excessively long, a solvent causes partial swelling of the original coating; if the mass content of solid of the coating is excessively low, the excessively low mass content of solid causes the swelling of the original coating; if the mass content of solid is excessively high, the excessively high mass content of solid affects an atomization effect during the spraying.

Preferably, in step (1), the dirt on the surface of the insulator is wiped off by using a dry flannel or an unwoven fabric.

Preferably, in step (2), the hydrophobicity is tested by using a hydrophobicity classification (HC) method; the color of the coating is determined by using a coating color chart; the coating color chart provides 9 colors that are separately represented by numbers 1-9; if a value is 1-5, it indicates that a state of the coating is relatively good; if a value is 6-9, it indicates that a state of the coating is relatively poor; and step (2) includes the following substeps:

(2.1) if the hydrophobicity is HC1-HC2, perform step (2.2); if the hydrophobicity is HC5-HC7, perform step (2.3); and if the hydrophobicity is HC3-HC4, perform step (2.4);

(2.2) if the color of the coating is 1-5, the insulator does not need to be coated, and if the color of the coating is 6-9, perform step (2.4);

(2.3) if the color of the coating is 1-5, perform step (2.4), and if the color of the coating is 6-9, the insulator cannot be recoated;

(2.4) the adhesion is tested by using a cross-cut test; if the adhesion is ISO4-ISO6, the insulator cannot be recoated; and if the adhesion is ISO0-ISO3, the insulator can be recoated.

Preferably, in substep (2.4), a position, close to the steel cap, on the upper surface of the insulator body is selected for the adhesion test.

Preferably, the 9 colors provided in the coating color chart are represented by values by using an RGB color space, and the numbers 1-9 are separately represented as follows:

|   | R | G | B |
|---|---|---|---|
| 1 | 147-152 | 68-78 | 55-64 |
| 2 | 153-157 | 79-87 | 65-74 |
| 3 | 158-162 | 88-98 | 75-84 |
| 4 | 163-167 | 99-107 | 85-94 |
| 5 | 168-172 | 108-118 | 95-104 |
| 6 | 173-177 | 119-127 | 105-114 |
| 7 | 178-182 | 128-138 | 115-124 |
| 8 | 183-187 | 139-147 | 125-134 |
| 9 | 188-192 | 148-158 | 135-144 |

Preferably, the numbers 1-9 are separately represented as follows:

|   | R | G | B |
|---|---|---|---|
| 1 | 150 | 73 | 60 |
| 2 | 155 | 83 | 70 |
| 3 | 160 | 93 | 80 |
| 4 | 165 | 103 | 90 |
| 5 | 170 | 113 | 100 |
| 6 | 175 | 123 | 110 |
| 7 | 180 | 133 | 120 |
| 8 | 185 | 143 | 130 |
| 9 | 190 | 153 | 140 |

Preferably, when the hydrophobicity test is performed by using the HC method, a watering can is used to spray water, so as to enable water drops to cover all the surface of the insulator, and a part with relatively poor hydrophobicity is selected for the hydrophobicity test.

With the present application, an insulator coated with an RTV anti-pollution flashover coating can be recoated. After coating is performed according to the procedure of the present application, a newly coated anti-pollution flashover coating can be closely adhered to a surface of the insulator, swelling does not occur, adhesion of the coating with respect to the insulator is not reduced, the hydrophobicity of the surface is recovered, and non-reduction of a pollution flashover voltage of the insulator is ensured.

BRIEF DESCRIPTION OF THE DRAWINGS

The present disclosure will become more fully understood from the detailed description given herein below for illustration only, and thus are not limitative of the present disclosure, and wherein.

DETAILED DESCRIPTION

The present application is further described below with reference to preferred implementation manners.

Figure 1:
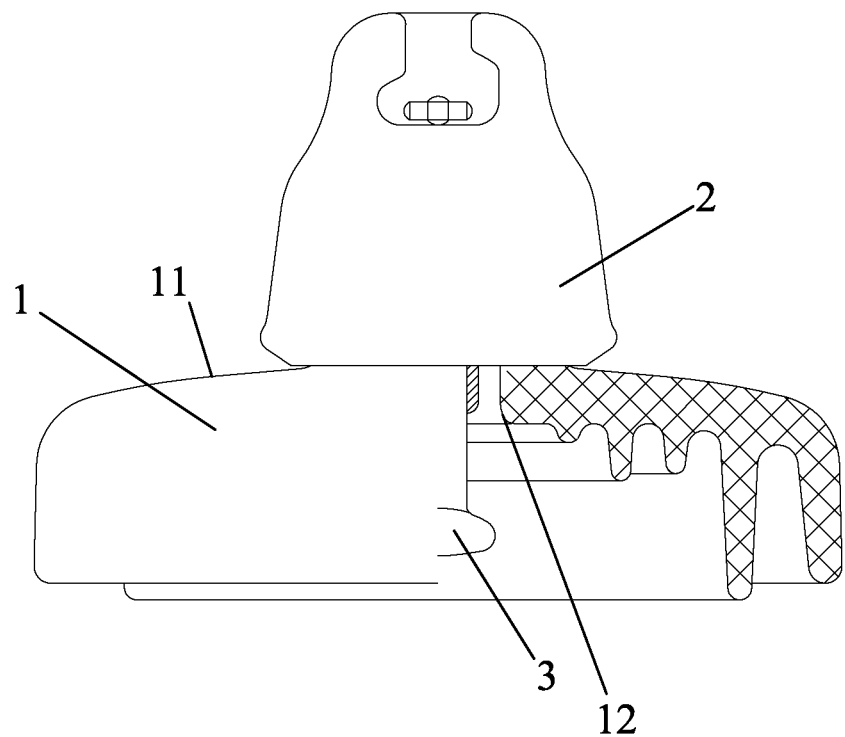
FIG. 1 is a semi-sectional view of an insulator according to an embodiment of the present application.
Figure 2:
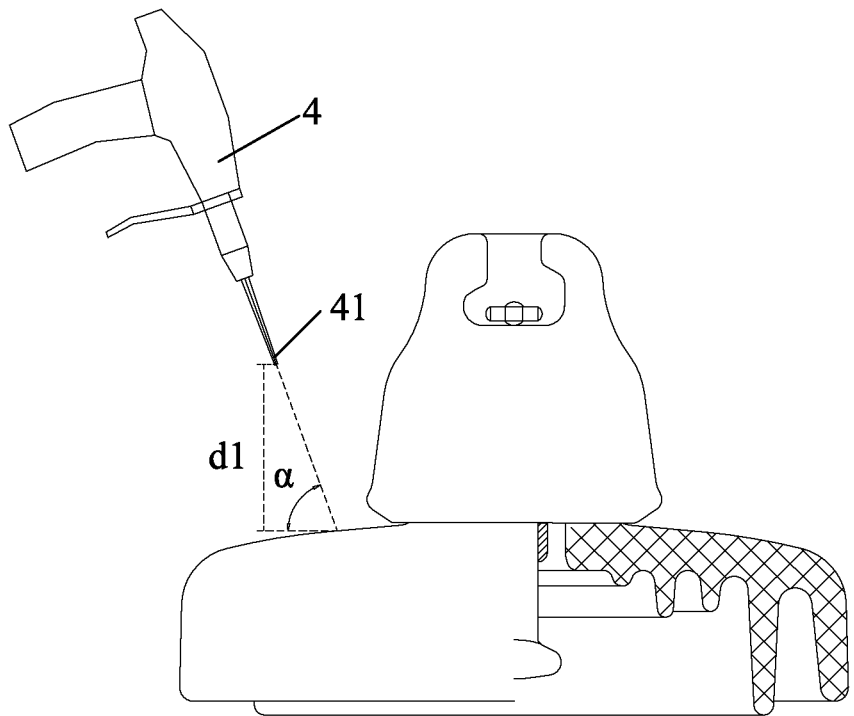
FIG. 2 is a view of the relative position between the spray gun and the insulator when the upper surface of the insulator body is sprayed with the RTV anti-pollution flashover coating by using a spray gun according to an embodiment of the present application.
Figure 3:
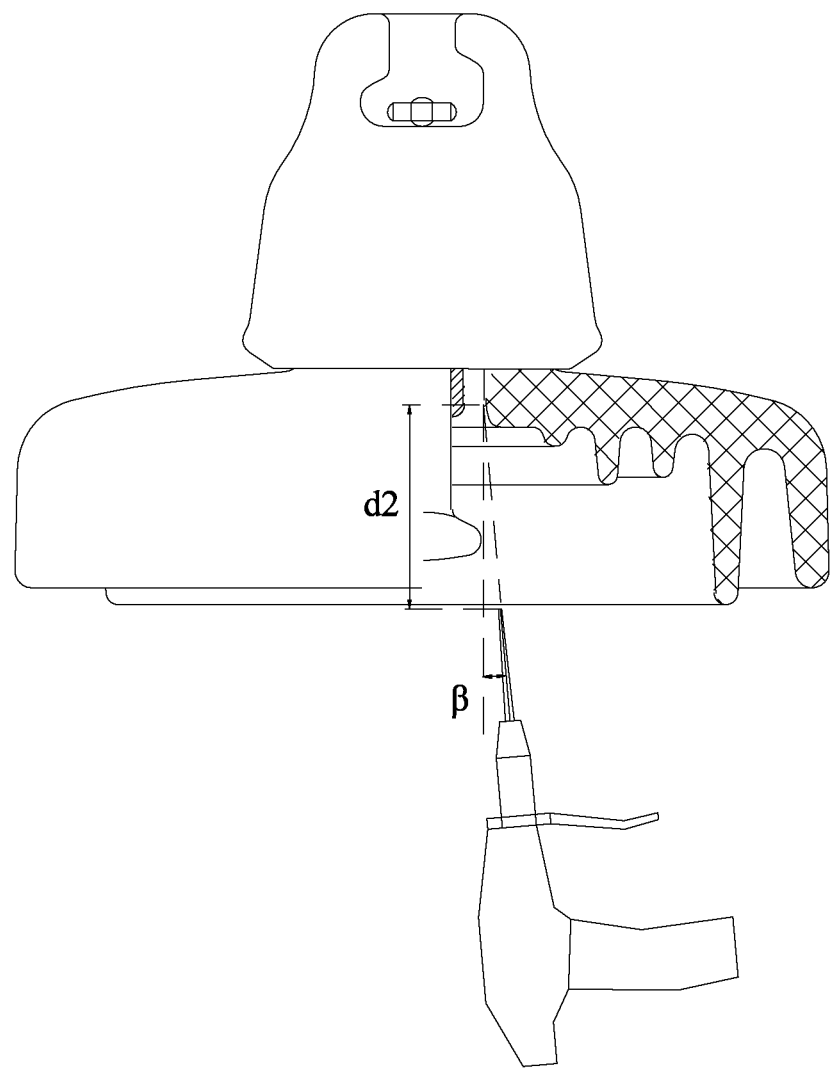
FIG. 3 is a view of the relative position between the spray gun and the insulator when the position of a seam formed by connecting the steel pin and the lower surface of the insulator body is sprayed with an RTV anti-pollution flashover coating by using a spray gun according to an embodiment of the present application.

The present application provides a method for recoating an RTV anti-pollution flashover coating on an insulator coated with the RTV anti-pollution flashover coating. In an embodiment, as shown in FIG. 1 the insulator includes an insulator body 1, a steel cap 2 connected to an upper surface 11 of the insulator body 1, and a steel pin 3 connected to a lower surface 12 of the insulator body 3. In a specific implementation manner, the method includes the following steps:

(1) wiping off dirt on a surface of the insulator;

(2) determining, according to a comprehensive evaluation of the hydrophobicity and adhesion of or a comprehensive evaluation of the hydrophobicity, color of the coating, and adhesion of an original coating of an RTV anti-pollution flashover coating on a surface of the insulator, whether the insulator can be recoated; and (3) applying coating as follows on an insulator that can be coated:

(3.1) when the insulator body and the position of a seam formed by connecting the steel cap and the upper surface of the insulator body are sprayed with the RTV anti-pollution flashover coating by using a spray gun, the pressure being 0.6±0.1 MPa, the distance between a nozzle of the spray gun and the surface to be sprayed of the insulator being 200±50 mm, the angle between an airflow axis and the surface to be sprayed being 70°-90°, and the standing time at the same position during spraying being 1-2 s. As shown in FIG. 2 which is a view of the relative position between the spray gun and the insulator when the upper surface of the insulator body is sprayed with the RTV anti-pollution flashover coating by using a spray gun, wherein the distance d1 between a nozzle 41 of the spray gun 4 and the surface to be sprayed of the insulator is 200±50 mm, and the angle a between an airflow axis and the surface to be sprayed is 70°-90°; and (3.2) when the position of a seam formed by connecting the steel pin and the lower surface of the insulator body is sprayed with an RTV anti-pollution flashover coating by using a spray gun, the pressure being 0.6±0.1 MPa, the distance between a nozzle of the spray gun and the position of the seam being 100±30 mm, the angle between an airflow axis and the lower surface of the insulator body being 0°-20°, and the standing time at the same position during spraying being not greater than 1 s. As shown in FIG. 3 which is a view of the relative position between the spray gun and the insulator when the position of a seam formed by connecting the steel pin and the lower surface of the insulator body is sprayed with an RTV anti-pollution flashover coating by using a spray gun, wherein the distance d2 between a nozzle 41 of the spray gun 4 and the surface to be sprayed of the insulator is 100±30mm, and the angle β between an airflow axis and the surface to be sprayed is 0-20°.

In steps (3.1) and (3.2), the mass content of solid of the recoated RTV anti-pollution flashover coating is 55%-65%, spraying is performed at least twice, and the thickness of a newly coated coating of the RTV anti-pollution flashover coating is not less than 0.2 mm.

When selecting an insulator is performed, a part of insulators may be separately selected for testing from lines with different voltages, for example, in a line with a voltage of 110 kV, one insulator is selected from each string; in a line with a voltage of 220 kV, two insulators are selected from each string; and in each string, an insulator located at a high-voltage side is preferably selected. After an insulator is run for many years, a relatively severe dirt accumulation phenomenon occurs on a surface of an RTV anti-pollution flashover coating on a surface of the insulator. A dirt layer significantly affects adhesion of a newly coated RTV anti-pollution flashover coating with respect to an original coating. Preferably, the dirt on the surface of the insulator is wiped off by using a dry flannel or an unwoven fabric. Then, a running state of the insulator is determined according to results of tests performed on an original coating of the RTV anti-pollution flashover coating of the insulator. The running state can be classified into three types: 1. the running state is good, and recoating is not required; 2. the running state is relatively poor, but the running state may be recovered to a relatively good state after an insulator is recoated by using the method of the present application; and 3. the running state is poor, and an insulator cannot be recoated and shall be replaced. In the present application, preferably, the running state of an insulator is determined by using the following steps.

In step (2), the hydrophobicity is tested by using an HC method; the color of the coating is determined by using a coating color chart; the coating color chart provides 9 colors that are separately represented by numbers 1-9; a smaller number indicates a better state of a coating, and a larger number indicates a poorer state of a coating; if a value is 1-5, it indicates that a state of a coating is relatively good; if a value is 6-9, it indicates that a state of a coating is relatively poor. Step (2) includes the following substeps:

(2.1) if the hydrophobicity is HC1-HC2, perform step (2.2); if the hydrophobicity is HC5-HC7, perform step (2.3); and if the hydrophobicity is HC3-HC4, perform step (2.4);

(2.2) if the color of a coating is 1-5, the insulator does not need to be coated, and if the color of a coating is 6-9, perform step (2.4);

(2.3) if the color of a coating is 1-5, perform step (2.4), and if the color of a coating is 6-9, the insulator cannot be recoated;

(2.4) the adhesion is tested by using a cross-cut test; if the adhesion is ISO4-ISO6, the insulator cannot be recoated; and if the adhesion is ISO0-ISO3, the insulator can be recoated.

More preferably, in substep (2.4), a position, close to the steel cap, on the upper surface of the insulator body is selected for the adhesion test. When the adhesion test is performed, water drops or a water film on the surface of the original coating may be gently wiped by using degreasing cotton, and wiping hard is not preferable since it may affect the adhesion of the original coating with respect to the surface of the insulator. The 9 colors provided in the coating color chart are represented by values by using an RGB color space (the values of RGB below are all integers), and the numbers 1-9 are separately represented as follows:

|   | R | G | B |
|---|---|---|---|
| 1 | 147-152 | 68-78 | 55-64 |
| 2 | 153-157 | 79-87 | 65-74 |
| 3 | 158-162 | 88-98 | 75-84 |
| 4 | 163-167 | 99-107 | 85-94 |
| 5 | 168-172 | 108-118 | 95-104 |
| 6 | 173-177 | 119-127 | 105-114 |
| 7 | 178-182 | 128-138 | 115-124 |
| 8 | 183-187 | 139-147 | 125-134 |
| 9 | 188-192 | 148-158 | 135-144 |

More preferably, the numbers 1-9 are separately represented as follows:

|   | R | G | B |
|---|---|---|---|
| 1 | 150 | 73 | 60 |
| 2 | 155 | 83 | 70 |
| 3 | 160 | 93 | 80 |
| 4 | 165 | 103 | 90 |
| 5 | 170 | 113 | 100 |
| 6 | 175 | 123 | 110 |
| 7 | 180 | 133 | 120 |
| 8 | 185 | 143 | 130 |
| 9 | 190 | 153 | 140 |

According to the RGB values in the above table, the coating color chart may be drawn by using drawing software (e.g. Photoshop), so as to determine the color of a coating. When the hydrophobicity test is performed by using the HC method, a watering can is used to spray water, so as to enable water drops to cover all the surface of the insulator, and a part with relatively poor hydrophobicity is selected for the hydrophobicity test according to a common determining method in the art. Alternatively, the hydrophobicity test is separately performed on an upper surface and a lower surface of an insulator body, and a poorer test result is selected as a final hydrophobicity value.

With regard to the mass content of solid of an RTV anti-pollution flashover coating, the content of solid in a recoated RTV anti-pollution flashover coating may be first tested according to *GB/T1725-2007, Paints, Varnishes and Plastics—Determination of Nonvolatile-matter Content*.

A coating recoated by using the method of the present application satisfies the following conditions: 1. the coating covers all the surface of an insulator, and there is no missed part; 2. stacking, suspension, and flowing phenomena do not occur on the surface of the coating; 3. the surface of the coating is kept smooth, and there is no visible uneven phenomenon; 4. the hydrophobicity: the hydrophobicity is tested by using the HC method, and may achieve HC1-HC2; 5. the thickness of the coating: slicing and sampling are performed on the coating, the thickness of each sample is measured, the total thickness (the sum of the thickness of the new coating and the thickness of the original coating) is not less than 0.35 mm, sampling is separately performed on an edge of an upper surface of, and a position, close to a steel cap, of the upper surface of an insulator body, and a sample is preferably not less than 10×10 mm; and 6. the adhesion: a cross-cut test is performed at a position, close to the steel cap, on the upper surface of the insulator body, and the adhesion level is ISO0-ISO2. The foregoing six test results obtained in the present application may be used as acceptance criteria of the recoating. During an acceptance check, as long as one test result fails to meet requirements, it indicates that a coating process fails to meet requirements. A running state of the recoated insulator of the present application is tested by simulating in a laboratory that the insulator is in a heavily foggy condition for a long time, and a result thereof is that: a leakage current value of the surface of the recoated insulator is kept below 1 mA, and the recoated insulator has a good anti-pollution flashover capability.

The foregoing content further describes the present application with reference to specific preferred implementation manners, and specific implementations of the present application shall not be considered to be limited thereto. Several equivalent replacements or obvious deformations with the same properties or applications may be further made by a person skilled in the art without departing from the thought of the present application, and shall be deemed to be within the protection scope of the present application.

What is claimed is:

1. A method for recoating an RTV anti-pollution flashover coating on an insulator that is coated with an original RTV anti-pollution flashover coating and that includes an insulator body, a steel cap connected to an upper surface of the insulator body, and a steel pin connected to a lower surface of the insulator body, comprising:
   (1) wiping off dirt on a surface of the insulator;
   (2) determining whether the insulator can be recoated, according to a comprehensive evaluation of hydrophobicity and adhesion of the original RTV anti-pollution flashover coating or a comprehensive evaluation of hydrophobicity, color, and adhesion of the original RTV anti-pollution flashover coating; and
   (3) recoating the RTV anti-pollution flashover coating on the insulator as follows:
      (3.1) spraying the insulator body and a seam formed by connecting the steel cap and the upper surface of the insulator body with the RTV anti-pollution flashover coating using a spray gun, at a pressure being 0.6±0.1 MPa, a distance between a nozzle of the spray gun and the surface to be sprayed on the insulator being 200±50 mm, an angle between an airflow axis and the surface of the insulator to be sprayed being 70°-90°, and a standing time at a same position during spraying being 1-2 s; and
      (3.2) spraying of a seam formed by connecting the steel pin and the lower surface of the insulator body with the RTV anti-pollution flashover coating using a spray gun at a pressure being 0.6±0.1 MPa, a distance between a nozzle of the spray gun and the seam being 100±30 mm, an angle between an airflow axis and the lower surface of the insulator body being 0°-20°, and a standing time at a same position during spraying being not greater than 1 s,
   wherein, in steps (3.1) and (3.2), a mass content of solid of the RTV anti-pollution flashover coating is 55%-65%, the spraying is performed at least twice, and a thickness of the RTV anti-pollution flashover coating is not less than 0.2 mm;
   wherein, in step (2), the hydrophobicity of the original RTV anti-pollution flashover coating on the surface of the insulator is determined by using a hydrophobicity classification (HC) method in accordance with IEC/TS 62073-2003 Standard; the color of the original RTV anti-pollution flashover coating on the surface of the insulator is graded in accordance with a coating color chart that has color grades in a range of 1-9; and the step (2) includes the following substeps:
      (2.1) performing step (2.2) when the hydrophobicity is HC1-HC2, performing step (2.3) when the hydrophobicity is HC5-HC7, and performing step (2.4) when the hydrophobicity is HC3-HC4;
      (2.2) performing step (2.4) when the color of the original RTV anti-pollution flashover coating has a color grade of 6-9; the insulator does not need to be recoated when the color of the original RTV anti-pollution flashover coating has a color grade of 1-5;
      (2.3) performing step (2.4) when the color of the original RTV anti-pollution flashover coating has a grade of 1-5, the insulator does not need to be recoated when the color of the original RTV anti-pollution flashover coating has a grade of 6-9; and
      (2.4) testing adhesion using a cross-cut test when the adhesion isISO4-
         ISO6, the insulator cannot be recoated, and when the adhesion is ISO0-
         ISO3, the insulator can be recoated;
   wherein the coating color chart is based on RGB color model and is as follows,

| Grade | R | G | B |
|---|---|---|---|
| 1 | 147-152 | 68-78 | 55-64 |
| 2 | 153-157 | 79-87 | 65-74 |
| 3 | 158-162 | 88-98 | 75-84 |
| 4 | 163-167 | 99-107 | 85-94 |
| 5 | 168-172 | 108-118 | 95-104 |
| 6 | 173-177 | 119-127 | 105-114 |
| 7 | 178-182 | 128-138 | 115-124 |
| 8 | 183-187 | 139-147 | 125-134 |
| 9 | 188-192 | 148-158 | 135-144. |

2. The method according to claim 1, wherein, in step (1), the dirt on the surface of the insulator is wiped off using a dry flannel or an unwoven fabric.

3. The method according to claim 1, wherein, in substep (2.4), a position close to the steel cap on the upper surface of the insulator body is selected for the adhesion test.

4. The method according to claim 1, wherein the coating color chart is as follows:

| Grade | R | G | B |
|---|---|---|---|
| 1 | 150 | 73 | 60 |
| 2 | 155 | 83 | 70 |
| 3 | 160 | 93 | 80 |
| 4 | 165 | 103 | 90 |
| 5 | 170 | 113 | 100 |
| 6 | 175 | 123 | 110 |
| 7 | 180 | 133 | 120 |
| 8 | 185 | 143 | 130 |
| 9 | 190 | 153 | 140. |

5. The method according to claim 1, wherein the hydrophobicity test is performed using the HC method wherein water drops are sprayed on surfaces of the insulator, and part of the surfaces having relatively poor hydrophobicity is selected for the hydrophobicity test.

* * * * *